(12) United States Patent
Endo et al.

(10) Patent No.: US 8,767,059 B2
(45) Date of Patent: Jul. 1, 2014

(54) ELECTRONIC ENDOSCOPE

(75) Inventors: Azuchi Endo, Kanagawa (JP); Akihiko Erikawa, Kanagawa (JP); Takayuki Iida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 308 days.

(21) Appl. No.: 12/892,712

(22) Filed: Sep. 28, 2010

(65) Prior Publication Data

US 2011/0074942 A1 Mar. 31, 2011

(30) Foreign Application Priority Data

Sep. 29, 2009 (JP) ............................... P2009-225404
Mar. 29, 2010 (JP) ............................... P2010-076461

(51) Int. Cl.
*A61B 1/04* (2006.01)
*A61B 1/06* (2006.01)

(52) U.S. Cl.
USPC ........................................... 348/68; 600/109

(58) Field of Classification Search
None
See application file for complete search history.

(56) References Cited

U.S. PATENT DOCUMENTS

| | | | |
|---|---|---|---|
| 6,099,466 A | 8/2000 | Sano et al. | |
| 6,395,576 B1 | 5/2002 | Chang et al. | |
| 6,471,636 B1* | 10/2002 | Sano et al. | 600/109 |
| 6,537,211 B1 | 3/2003 | Wang et al. | |
| 2002/0035330 A1* | 3/2002 | Cline et al. | 600/476 |
| 2003/0050532 A1 | 3/2003 | Doguchi | |
| 2004/0186351 A1* | 9/2004 | Imaizumi et al. | 600/160 |
| 2005/0154319 A1* | 7/2005 | Cline et al. | 600/478 |
| 2006/0241499 A1* | 10/2006 | Irion et al. | 600/476 |
| 2006/0247537 A1 | 11/2006 | Matsumoto | |
| 2007/0015963 A1* | 1/2007 | Fengler et al. | 600/109 |
| 2007/0093691 A1* | 4/2007 | Kobayashi | 600/180 |
| 2008/0027278 A1 | 1/2008 | Mizuno | |

FOREIGN PATENT DOCUMENTS

| | | |
|---|---|---|
| EP | 1 099 405 A1 | 5/2001 |
| JP | 08-140928 | 6/1996 |
| JP | 09-070384 | 3/1997 |
| JP | 2003-079570 | 3/2003 |
| JP | 2006-296635 A | 11/2006 |
| JP | 2008-29621 A | 2/2008 |
| WO | WO 02/07587 A2 | 1/2002 |

OTHER PUBLICATIONS

European Search Report dated Dec. 17, 2010.
Japanese Office Action dated May 28, 2013 with partial English translation thereof.

* cited by examiner

*Primary Examiner* — Joseph Ustaris
*Assistant Examiner* — Ellyar Y Barazesh
(74) *Attorney, Agent, or Firm* — McGinn IP Law Group, PLLC

(57) ABSTRACT

An electronic endoscope includes an illumination unit, an imaging unit and an image generating unit. The illumination unit switches among plural light beams having different spectra so as to illuminate a subject. The light beams include white light and excitation light for exciting the subject to produce fluorescence. The imaging unit includes a solid-state imaging device, and an objective optical system. The objective optical system guides, to the solid-state imaging device, light returning from the subject which the illumination unit illuminates. The image generating unit generates image data based on image signals output from the imaging unit. The solid-state imaging device further includes a sensitivity adjusting unit that only lowers sensitivity, to the excitation light, of pixels which are sensitive to the fluorescence among a plurality of pixels of the solid-state imaging device. The light guided by the objective optical system is incident directly onto the solid-state imaging device.

15 Claims, 9 Drawing Sheets

FIG. 11
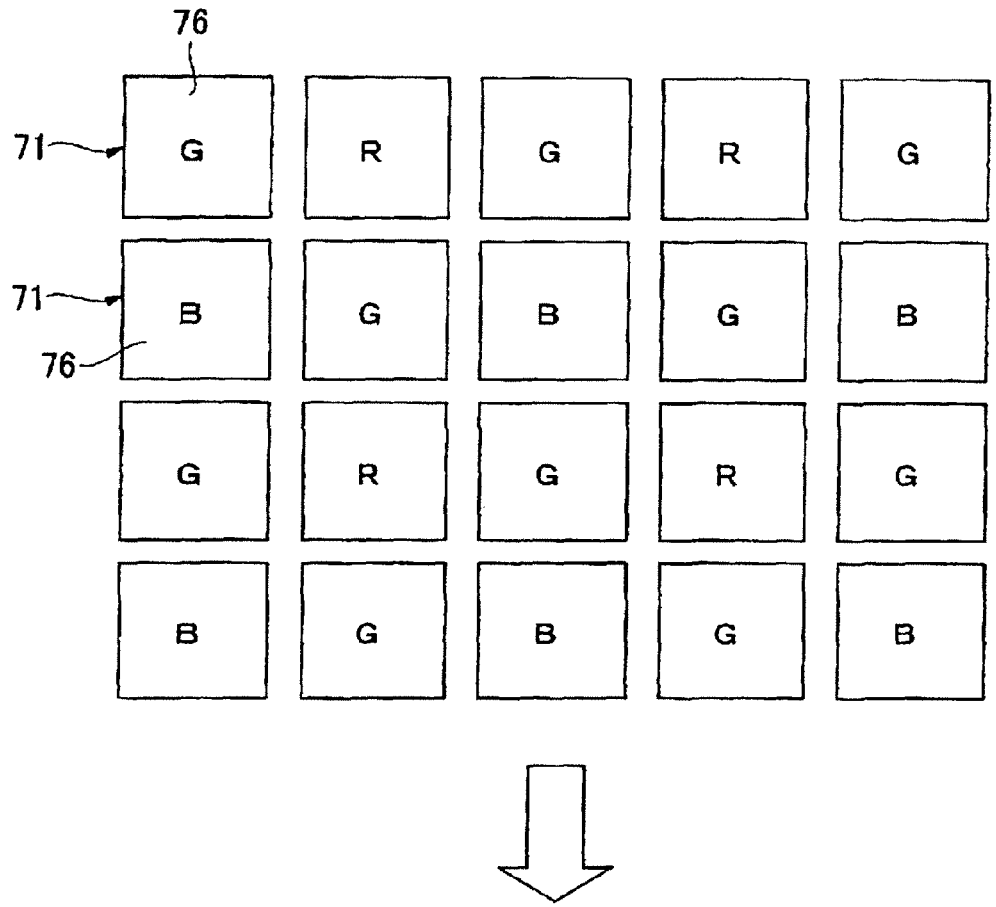
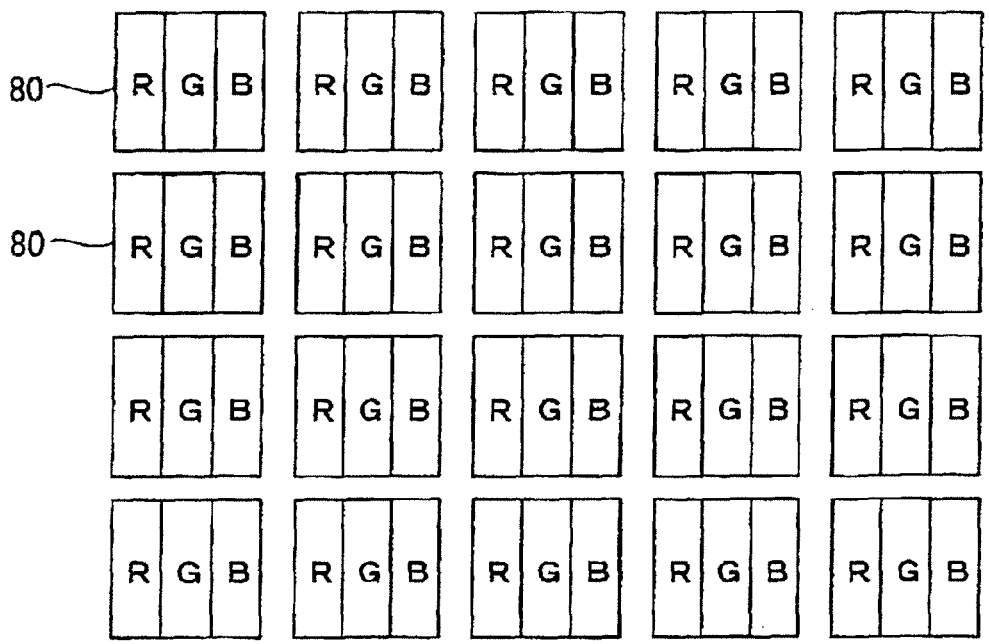

ELECTRONIC ENDOSCOPE

CROSS-REFERENCE TO RELATED APPLICATIONS

This application claims the benefit of Japanese Patent Application Nos. 2009-225404, filed Sep. 29, 2009, and 2010-76461, filed Mar. 29, 2010, the entire contents of which are hereby incorporated by reference, the same as if set forth at length.

BACKGROUND OF THE INVENTION

1. Field of the Invention

The present invention relates to an electronic endoscope.

2. Description of the Related Art

In recent years, the following technology is being put into practical use. That is, an electronic endoscope having a solid-state imaging device has been used to diagnose lesions of living tissues based on images obtained by applying excitation light onto a site, under observation, of a living tissue and imaging autofluorescence produced in the living tissue by the excitation light or fluorescence of an agent injected into a living body.

With respect to the autofluorescence of living tissue, when excitation light at a wavelength of about 405 nm is applied onto the living tissue, for example, normal tissue will produce green fluorescence at a wavelength of about 520 nm. In contrast, a lesion tissue such as cancer will not produce fluorescence or the fluorescence produced will be weak. Therefore, the lesion can be diagnosed.

With respect to the fluorescence of the agents, fluorescent materials such as hematoporphyrin derivatives and ALA (δ-aminolevulinic acid) are used. These fluorescent materials will produce red fluorescence at a wavelength of about 630 nm when excitation light at a wavelength of about 405 nm is applied thereto. These fluorescent materials tend to accumulate in lesion tissues such as cancer. Therefore, the lesion can be diagnosed.

Various types of electronic endoscopes have been proposed to perform the above-mentioned fluorescence observation and normal observation to apply white light onto a living tissue and image reflected/scattered light (for example, see JP Hei.8-140928 A (corresponding to U.S. Pat. Nos. 6,099,466 and 6,471,636), JP Hei.9-70384 A (corresponding to U.S. Pat. Nos. 6,099,466 and 6,471,636) and JP 2003-79570 A (corresponding to US 2003/0050532 A).

JP Hei.8-140928 A describes an electronic endoscope provided with two solid-state imaging devices at a distal end of the endoscope for normal observation and fluorescence observation.

JP Hei.9-70384 A describes an electronic endoscope provided with two solid-state imaging device at a distal end of the endoscope for normal observation and fluorescence observation. A supersensitive solid-state imaging device is used as the solid-state imaging device for fluorescence observation.

JP 2003-79570 A describes an electronic endoscope using one solid-state imaging device with a variable charge multiplication factor. The one imaging device performs normal observation and fluorescence observation by changing the charge multiplication factor between the normal observation and the fluorescence observation.

When two solid-state imaging device for the normal observation and the fluorescence observation are provided at the distal end of the endoscope as described in JP Hei.8-140928 A and JP Hei.9-70384 A, it is difficult to reduce a size of the distal end of the endoscope.

Furthermore, an intensity of the autofluorescence of the living tissue or the fluorescence of the agent is extremely weak compared to that of the excitation light reflected/scattered by the living tissue. Therefore, the endoscopes described in JP Hei.8-140928 A and JP Hei.9-70384 A have a filter for passing only the fluorescence which is disposed between the solid-state imaging device for fluorescence observation and an objective optical system for guiding feedback light (reflected/scattered light or fluorescence) from the living tissue to the solid-state imaging device. The endoscope described in JP 2003-79570 A has a filter for cutting the excitation light which is disposed between the solid-state imaging device and an objective optical system.

In the endoscope described in JP 2003-79570 A which performs normal observation and fluorescence observation with the same solid-state imaging device, since the excitation light cutting filter is disposed between the solid-state imaging device and the objective optical system, color information corresponding to the wavelength of the excitation light is lost in normal observation.

Furthermore, the intensity of the autofluorescence of the living tissue or the fluorescence of the agent is extremely weak even compared to that of the reflected/scattered light imaged in normal observation. Then, in order to obtain images having appropriate brightness for both the normal observation and the fluorescence observation, the endoscope described in JP Hei.9-70384 A uses a supersensitive solid-state imaging device for the fluorescence observation, while that described in JP 2003-79570 A uses a solid-state imaging device with the variable charge multiplication factor. However, both of them are expensive.

SUMMARY OF THE INVENTION

One embodiment of the present invention has been made in view of the above-described circumstances, and provides an electronic endoscope which performs normal observation and fluorescence observation with the same solid-state imaging device and is capable of avoiding that color information is lost in normal observation.

According to an aspect of the invention, an electronic endoscope includes an illumination unit, an imaging unit and an image generating unit. The illumination unit switches among a plurality of light beams having different spectra from each other so as to illuminate a subject. The light beams include at least white light and excitation light for exciting the subject to produce fluorescence. The imaging unit includes a solid-state imaging device and an objective optical system. The objective optical system guides, to the solid-state imaging device, light returning from the subject which the illumination unit illuminates. The image generating unit generates image data based on image signals output from the imaging unit. The solid-state imaging device further includes a sensitivity adjusting unit that only lowers sensitivity, to the excitation light, of pixels which are sensitive to the fluorescence among a plurality of pixels of the solid-state imaging device. The light guided by the objective optical system is incident directly onto the solid-state imaging device.

With the above configurations, normal observation and fluorescence observation are performed with the same solid-state imaging device by having the illumination section to switch between the white light and the excitation light for application. By only lowering the sensitivities, to the excitation light, of the pixels which are sensitive to the fluorescence produced by the subject onto which the excitation light is applied, and making the light guided by the objective optical system incident directly onto the solid-state imaging element, the loss of the color information corresponding to the excitation light can be avoided in the normal observation, and the fluorescence can be imaged while the pixel saturation caused by the excitation light in the fluorescence observation is prevented.

BRIEF DESCRIPTION OF THE DRAWINGS

FIG. 11 is a diagram which schematically illustrates the structure of image data generated by an image generating section of the electronic endoscope in FIG. 1.

DETAILED DESCRIPTION OF EMBODIMENTS OF THE INVENTION

Figure 1:
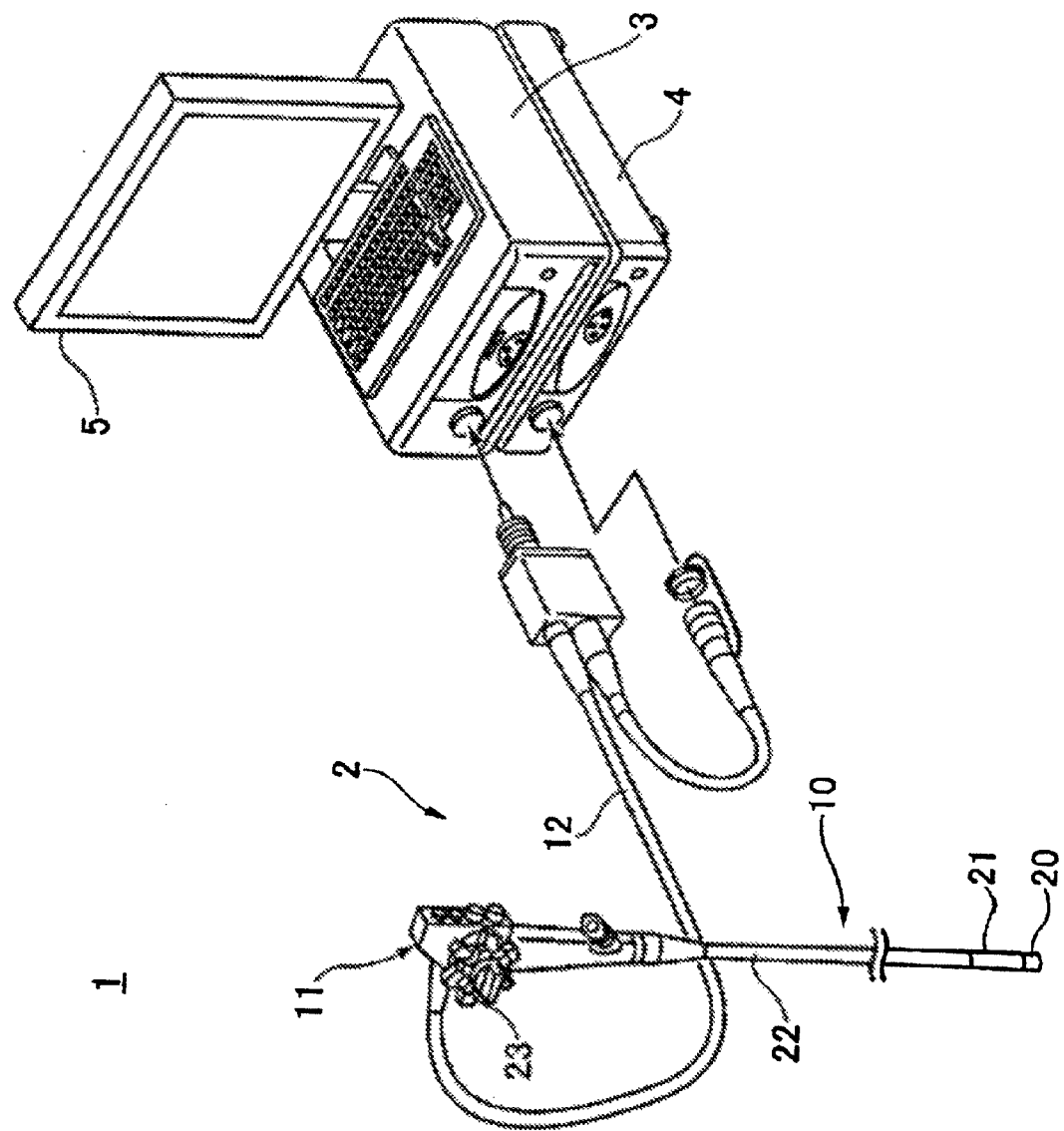
FIG. 1 is a diagram which illustrates an example of an electronic endoscope, for explaining an embodiment of the present invention.

FIG. 1 illustrates an example of an electronic endoscope.

As shown in FIG. 1, the electronic endoscope 1 includes an endoscope body 2, a light source unit 3 and a processor unit 4 which are connected to the endoscope body 2, and a monitor 5 which is connected to the processor unit 4.

The endoscope body 2 has an insertion portion 10 which is to be inserted into a subject, an operation portion 11 from which the insertion portion 10 extends, and a universal cord 12 which extends from the operation portion 11. The endoscope body 2 is connected to the light source unit 3 and the processor unit 4 via the universal cord 12.

The insertion portion 10 has a distal end portion 20, a bent portion 21, and a flexible portion 22. The bent portion 21 extends from a base end of the distal end portion 20, and can be bent vertically and horizontally. The flexible portion 22 connects the bent portion 21 and the operation portion 11.

A bending operation portion 23 which operates the bending of the bent portion 21 is provided on the operation portion 11. The bending operation portion 23 has two bending operation knobs to be rotated. One of the bending operation knobs operates the bent portion 21 to vertically bend, while the other operates the bent portion 21 to horizontally bend.

Figure 2:
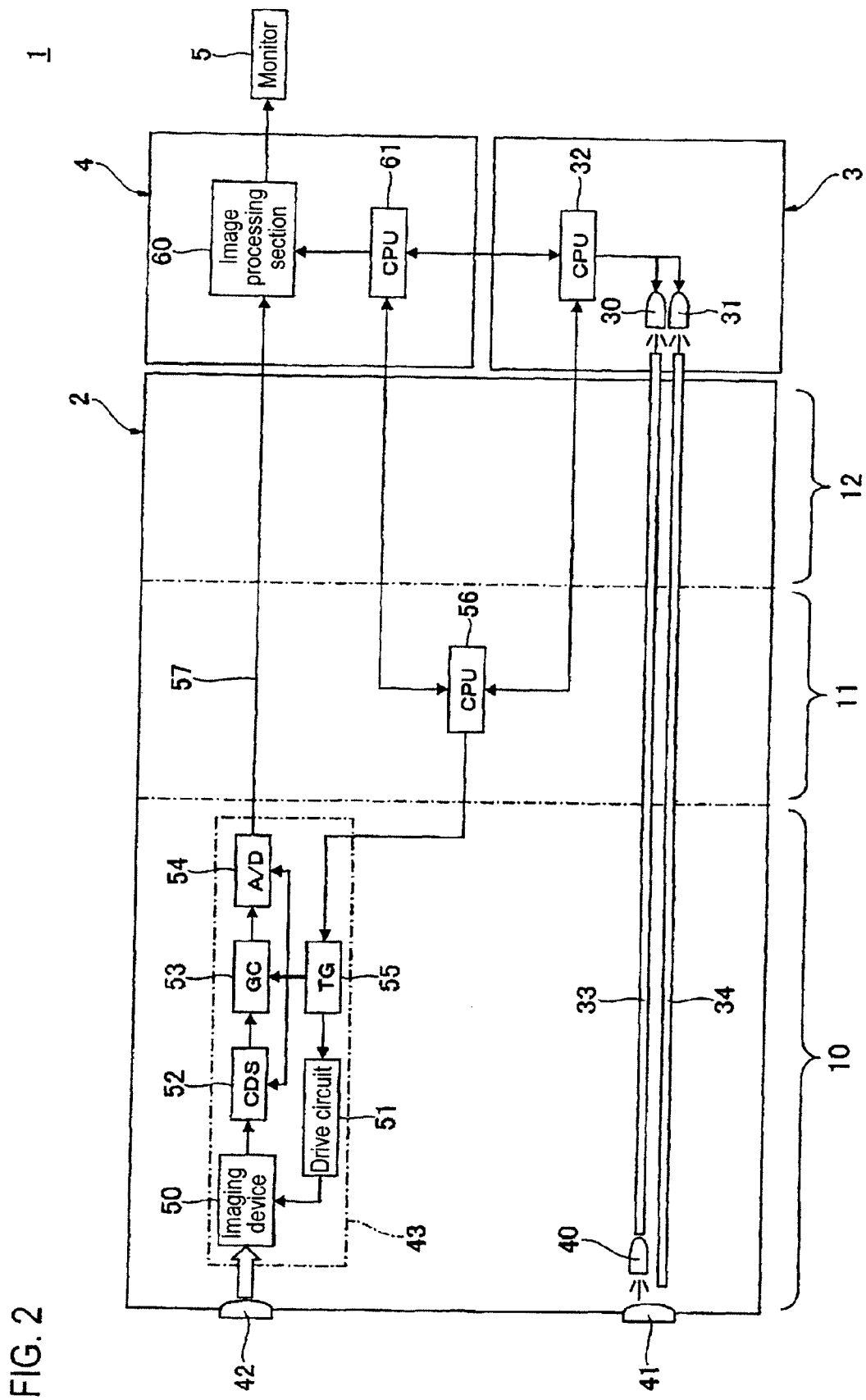
FIG. 2 is a diagram which illustrates, in detail, the electronic endoscope shown in FIG. 1.

FIG. 2 illustrates, in detail the electronic endoscope 1.

As shown in FIG. 2, the light source unit 3 has a first light source 30, a second light source 31, and a CPU 32.

The first light source 30 has a semiconductor light emitting element which emits blue laser light having its center wavelength at about 455 nm. The blue laser light emitted from the first light source 30 excites a phosphor which will be described later and which is provided at the distal end portion 20 of the insertion portion 10 of the endoscope body 2 (see FIG. 1), to produce white light for normal observation in conjunction with fluorescence produced in the phosphor.

The second light source 31 has a semiconductor light emitting element which emits blue laser light having its center wavelength at about 405 nm. The blue laser light emitted from the second light source 31 is excitation light for fluorescence observation and causes the subject to produce fluorescence. Hereinafter, the blue laser light emitted from the second light source 31 may be referred to as the "excitation light".

The above-mentioned semiconductor light emitting elements used in the first light source 30 and the second light source 31 are, for example, broad-area InGaN-based laser diodes, InGaNAs-based laser diodes, and GaNAs-based laser diodes.

CPU 32 controls turning on/off of the first light source 30 and second light source 31.

The blue laser light emitted from the first light source 30 is incident on one end of an optical fiber 33, and the excitation light emitted from the second light source 31 is incident on one end of an optical fiber 34. These optical fibers 33, 34 reach the distal end 20 of the insertion portion 10 via the universal cord 12 and operation portion 11 of the endoscope body 2. The blue laser light emitted from the first light source 30 and the excitation light emitted from the second light source 31 are transmitted to the distal end 20 by the optical fibers 33 and 34, respectively.

The optical fibers 33 and 34 are multimode fibers. For example, the optical fibers 33 and 34 may be thin fiber cables having a diameter of 0.3 to 0.5 mm which includes a core diameter of 105 μm, a cladding diameter of 125 μm, and a protection layer serving as a sheath.

At the distal end portion 20 of the insertion portion 10 of the endoscope body 2 (see FIG. 1), a phosphor 40, an illumination optical system 41, an objective optical system 42, and an imaging unit 43 are provided.

The phosphor 40 is provided at a distal end portion of the optical fiber 33 for transmitting the blue laser light emitted from the first light source 30. This phosphor 40 has one or more kinds of fluorescent materials which absorb a part of the blue laser light from the first light source 30 and are excited to emit light in a range of green to yellow.

Examples of the fluorescent material includes a YAG ($Y_3Al_5O_{12}$)-based fluorescent material, and a BAM ($BaMgAl_{10}O_{17}$)-based fluorescent material. These fluorescent materials can prevent superposition the noise resulting from speckles due to the coherency of laser light which may harm imaging, and flickers when moving images are displayed. In view of a refractive index difference between the fluorescent material of the phosphor and the fixing/curing resin serving as fillers, the phosphor 40 is preferably composed of fluorescent materials whose grain diameter relative to that of the fillers make them absorb infrared light weakly and scatter it strongly. Thus, the scatter effect is enhanced without decreasing the intensity of red or infrared lights, and the optical loss becomes small.

The green to yellow fluorescence produced by the phosphor 40 and the blue laser light from the first light source 30 which passes through the phosphor 40 and is not absorbed are combined and constitute white light. If a semiconductor light emitting element is used as an excitation light source as in this embodiment which has high luminous efficiency, white light having high intensity can be achieved, and an intensity of the white light can be easily adjusted. Furthermore, the change in color temperature of the white color and change in chromaticity of the white light can be kept small.

Here, the white light as referred to in this specification is not limited to light that contains strictly all wavelength components of visible light, but includes in a broad sense light containing certain wavebands such as R, G, and B, for example, light containing wavelength components ranging from green to led, and light containing wavelength components ranging from blue to green.

Figure 3:
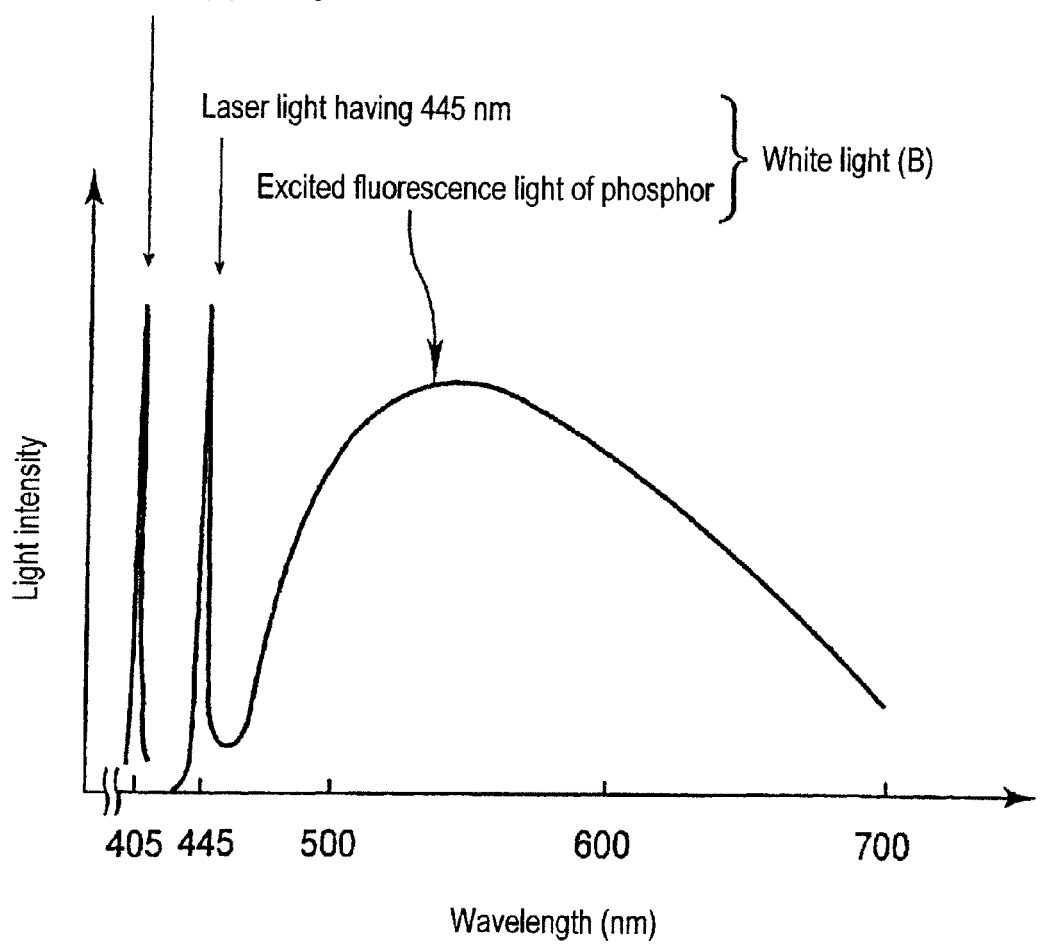
FIG. 3 is a diagram which illustrates the spectrum of white light emitted by the electronic endoscope in FIG. 1.

FIG. 3 illustrates the spectrum of the white light emitted by the electronic endoscope 1.

As shown in FIG. 3, the blue laser light emitted from the first light source 30 is indicated by an emission line having a center wavelength of about 445 nm. The fluorescence of the phosphor 40 excited by that blue laser light roughly has a spectral intensity distribution with luminous intensity increasing in the wavelength band of 450 nm to 700 nm. The profiles of the excited light and blue laser light form the above-mentioned white light.

Referring to FIG. 2 again, the white light and/or the excitation light emitted from the second light source 31 and transmitted by the optical fiber 34 is applied onto the subject through the illumination optical system 41. The feedback light from the subject onto which the white light and/or the excitation light is applied, i.e. the white light and/or the excitation light reflected/scattered by the subject, and the fluorescence produced by the subject onto which the excitation light is applied, is collected by the objective optical system 42 and is incident on the imaging unit 43.

The imaging unit 43 has a solid-state imaging device 50, a drive circuit 51 for the solid-state imaging device 50, a CDS (Correlated Double Sampling) circuit 52, a gain control circuit 53, an A/D converter 54, and a timing generator 55.

The solid-state imaging device 50 may be a CCD (Charge Coupled Device) imaging sensor, a CMOS (Complementary Metal-Oxide Semiconductor) imaging sensor, or the like. The feedback (reflected and/or scattered) light from the subject collected by the objective optical system 42 is incident from the objective optical system 42 directly (not through a fluorescence passing filter, an excitation light cutting filter, or the like of the related art) onto the solid-state imaging device 50, and forms an image on a light receiving area of the solid-state imaging device 50.

Charges corresponding to an amount of the received light are accumulated in pixels of the solid-state imaging device 50. The drive circuit 51 controls the accumulation of the charges in the pixels and reading-out of the charges accumulated in the pixels. The charges read out from the pixels are converted into voltages and output from the solid-state imaging device 50. Signals output from the solid-state imaging device 50 are subjected to the correlated double sampling in the CDS circuit 52, then to the gain correction by the gain control circuit 53, and to the A/D conversion by the A/D converter 54.

The timing generator (TG) 55 supplies clocks to the drive circuit 51, the CDS circuit 52, the gain control circuit 53, and the A/D converter 54, and controls a timing of the accumulation of the charges in the solid-state imaging device 50, a timing of the reading-out of the accumulated charges, a timing of the correlated double sampling by the CDS circuit 52, a timing of the gain correction by the gain control circuit 53, and a timing of the A/D conversion by the A/D converter 54.

The clock supply by the TG 55 is controlled by the CPU 56 provided in the endoscope body 2.

The imaging signals output from the A/D converter 54 are sent to the processor unit 4 via a signal line 57 which passes through the insertion portion 10, the operation portion 11, and the universal cord 12 to reach the processor unit 4.

The processor unit 4 has an image processing section 60, and a CPU 61 for controlling that image processing section 60. The image processing section 60 performs appropriate processing for the imaging signals to generate image data, and displays an image reproduced from those image data on the monitor 5.

The CPU 56, 32, 61, which are provided in the endoscope body 2, the light source unit 3, and the processor unit 4, respectively, communicate with each other to control the timings of illumination, imaging, and image generation.

The electronic endoscope 1 alternatively turns on the first light source 30 and the second light source 31 in the light source unit 3, to switch between the white light and the excitation light and apply one of the white light and the excitation light to the subject. Thereby, the normal observation and the fluorescence observation are performed.

In the normal observation, the first light source 30 in the light source unit 3 is turned on, and the white light is applied onto the subject. Then, images obtained by imaging the white light reflected/scattered by the subject are displayed on the monitor 5.

In the fluorescence observation, the second light source 31 in the light source unit 3 is turned on, and the excitation light having the center wavelength of about 405 nm is applied onto the subject. Then, images obtained by imaging the fluorescence produced by the subject onto which the excitation light is applied are displayed on the monitor 5. The autofluorescence of the subject is green fluorescence having a wavelength of about 520 nm, while the agent fluorescence is red fluorescence having a wavelength of about 630 nm.

Switching between the normal observation and the fluorescence observation may be implemented by, for example, providing a switching button in the operation portion 11 and operating that button, or switching may be made automatically in units of frames. In the case of switching automatically in units of frames, the images of the normal observation and the images of the fluorescence observation may can be displayed on the monitor 5 simultaneously and updated subsequently.

Furthermore, the electronic endoscope 1 may perform special light observation in addition to the normal observation and fluorescence observation. As special light observation, examples include the case where short-wavelength narrow-band light is used, the case where near-infrared light is used and the like. Since the short-wavelength narrow-band light reaches only the extremely shallow part of the surface layer of the subject, subtle changes on the surface of the subject may be recognized from images obtained by imaging its reflected/scattered light. Meanwhile, a deeper part of the subject may be recognized from images obtained by imaging the reflected/scattered light of the near-infrared light. The light source unit 3 may require a light source for emitting light corresponding to the special light observation. However, for the special light observation with short-wavelength narrow-band light, blue laser light having the center wavelength of 405 nm, i.e. the above-mentioned excitation light may be used, and a light source may be shared between the fluorescence observation and the special light observation.

Here, in the fluorescence observation, in addition to the fluorescence produced by the subject, the reflected/scattered light of the excitation light exciting that phosphor is also incident on the solid-state imaging device 50. As described above, the intensity of the autofluorescence of the subject and the fluorescence of the agents is extremely weak compared to that of the excitation light reflected/scattered by the subject. Therefore, among the plurality of pixels contained in the solid-state imaging device 50, measures are taken to lower the sensitivity, to the excitation light, of the pixels that are sensitive to the fluorescence.

Figure 4:
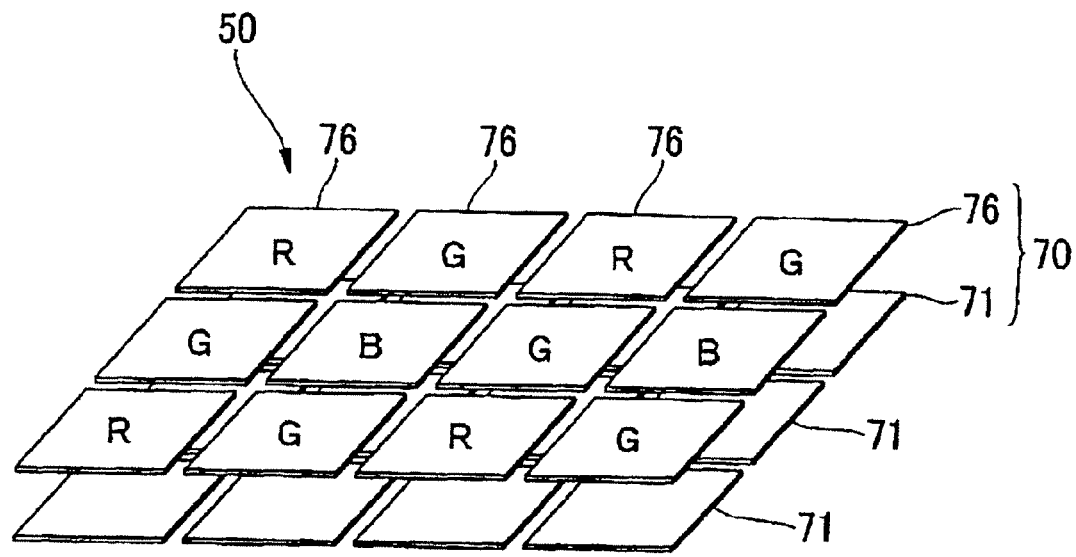
FIG. 4 is a diagram which schematically illustrates a solid-state imaging device shown in FIG. 2.

FIG. 4 schematically illustrates the solid-state imaging device 50.

As shown in FIG. 4, a plurality of pixels 70 are arranged on the solid-state imaging device 50. Each pixel 70 has a light receiving element 71, and a color filter 76 covering the light receiving element 71.

The color filter 76 of each pixel 71 allows one of red light, green light, and blue light to pass therethrough. Each pixel 71 is mainly sensitive to the light of the color corresponding to the color filter 76. Below, the color filter for allowing red light to pass therethrough will be referred to as a "R filter", the color filter for allowing green light to pass therethrough will be referred to as a "G filter", and the color filter for allowing blue light to pass therethrough will be referred to as a "B filter". In the illustrated example, the arrangement of the R filters, G filters, and B filters follows the so-called Bayer arrangement. However, the invention is not limited thereto. Here, an RGB primary-color-based imaging element having color filters for red, green, and blue is shown as an example. However, the invention is also not limited thereto. Instead, a CMY complementary-color-based imaging element having color filters for cyan (C), magenta (M), and yellow (Y), or a CMYG complementary-color-based imaging element further having color filters for green may be adopted.

In the case that the fluorescence is the autofluorescence of the subject, i.e. the green fluorescence at a wavelength of about 520 nm, the pixels sensitive to that fluorescence are those provided with the G filters. And, in the case where the fluorescence is the fluorescence of the agents, i.e. the red fluorescence at a wavelength of about 630 nm, the pixels sensitive to that fluorescence are those provided with the R filters.

As described above, the colors of the pixels to detect fluorescence vary depending on a difference between the autofluorescence and the agent fluorescence, the types of the fluorescent agents used for the agent fluorescence, and the like.

Here, the case where the fluorescence is the autofluorescence from the subject and the sensitivity to the excitation light of the pixels provided with the G filters sensitive to that fluorescence is lowered will be described first.

Figure 5:
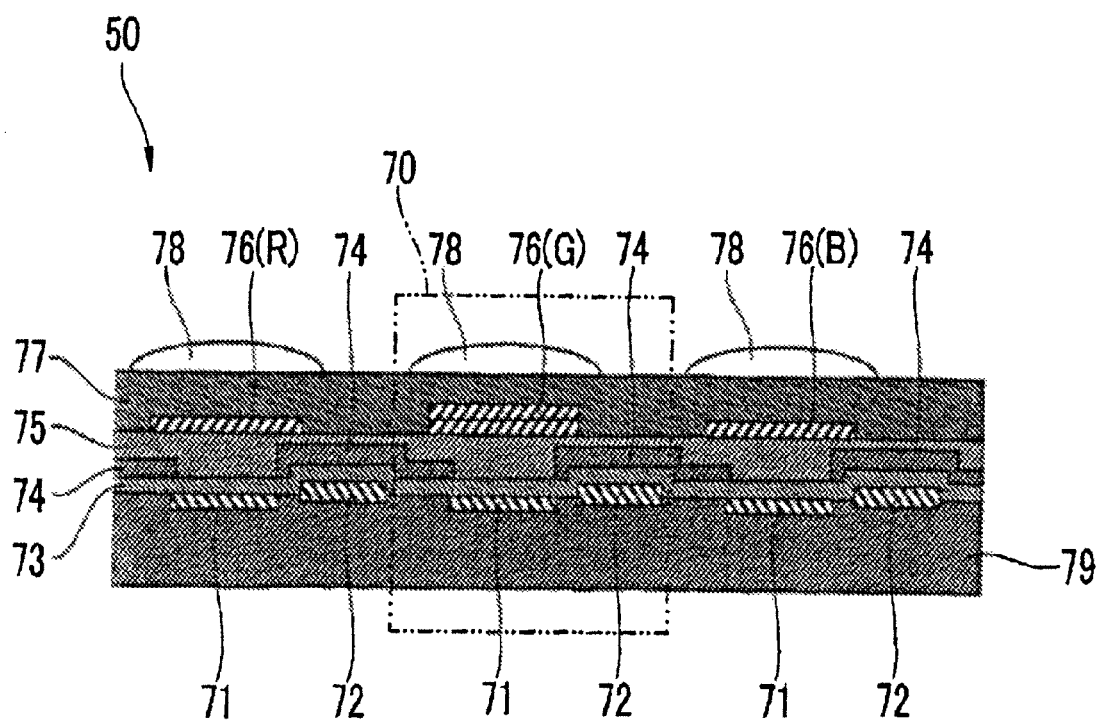
FIG. 5 is a diagram which illustrates, in detail, pixels contained in the solid-state imaging device shown in FIG. 4.

FIG. 5 illustrates, in detail, the pixels 70 contained in the solid-state imaging device 50.

As shown in FIG. 5, each pixel 70 has a light receiving element 71 and a charge transferring portion 72 which are formed on a surface of a semiconductor substrate 79. Each pixel 70 also has a surface protection film 73 covering the light receiving element 71 and the charge transferring portion 72, a light shielding film 74 formed on the protection film 73, a color filter 76 formed above the light shielding film 74 with a flattening insulation film 75 sandwiched therebetween, and a microlens 78 formed above the color filter 76 with a flattening insulation film 77 sandwiched therebetween. In the illustrated example, the R filter, the G filter, and the B filter are shown to be arranged in a line, but this is for the convenience of description. In fact, they follow the arrangement shown in FIG. 4.

Among the color filters 76, the G filter is formed thicker than the R filter and the B filter. In the illustrated example, the G filter is about 2 times as thick as the R filter and the B filter.

The R filter, G filter, and B filter typically are resists which are colored in response to the colors of the filters to be formed, and are formed by exposure in the photolithography method and the development process. Therefore, for example, by repeating resist-coating, exposing and developing plural times only for the G filter, it is possible to form the G filter to be thicker than the R filter and B filter.

Figure 6:
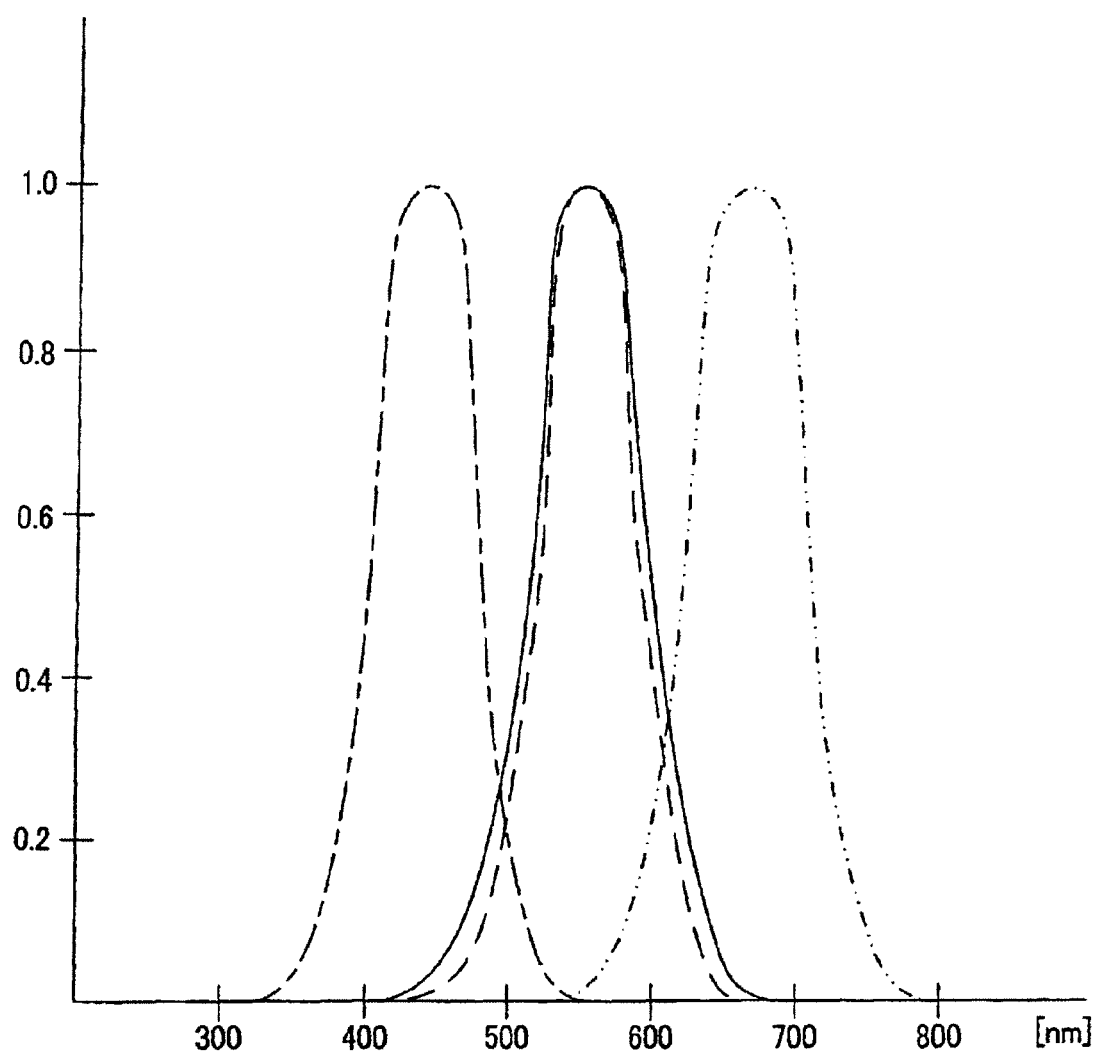
FIG. 6 is a diagram which illustrates the spectral sensitivity profiles of the pixels contained in the solid-state imaging device shown in FIG. 4.

FIG. 6 illustrates the spectral sensitivity profiles of the pixels contained in the solid-state imaging device 50.

In FIG. 6, the dashed line shows the sensitivity profile of the pixel provided with the G filter which is formed thicker than the R filter and the B filter, and the dot-dash line shows the sensitivity profile of the pixel provided with the B filter, and the dot-dot-dash line shows the sensitivity profile of the pixel provided with the R filter. Furthermore, the solid line shows the sensitivity profile of the pixel provided with the G filter which is formed in the same thickness as those of the R filter and B filter. Each line shows a relative sensitivity by normalizing the sensitivity at a wavelength where the sensitivity takes a maximum value as 1.

Typically, the sensitivity profile of each pixel is substantially mountain-shaped. The pixel provided with the G filter sensitive to the autofluorescence of the subject (the green fluorescence at a wavelength of about 520 nm) is also sensitive, although very weakly, to the excitation light (the blue laser light having the center wavelength of about 405 nm). However, as the G filter becomes thicker, its transmissivity becomes lower, and less amount of the excitation light reaches the light receiving element. As a result, the sensitivity to the incident excitation light of the pixel provided with the G filter becomes lower.

As the thickness of a filter changes, the sensitivity changes in response to the power of the change in the thickness. For example, it is assumed that the thickness T of the G filter is the same as the thickness t of the R filter and B filter (T=t), the sensitivity to fluorescence is 0.8, while the sensitivity to excitation light is 0.01. If the thickness T of the G filter is two times as large as the thickness t of the R filter and B filter (T=2 t), then the sensitivity to fluorescence becomes 0.64, while the sensitivity to excitation light becomes 0.0001. In this way, by thickening the filter of a pixel sensitive to fluorescence, the sensitivity to excitation light can be lowered dramatically compared to that to fluorescence.

Accordingly, even if the light guided by the objective optical system 42 is incident directly (not through the fluorescence passing filter, the excitation light cutting filter, or the like as in the related art) onto the solid-state imaging device 50, the fluorescence can still be imaged while the pixel saturation caused by the excitation light can be prevented during the fluorescence observation. By making the light guided by the objective optical system 42 be incident directly onto the solid-state imaging device 50, the loss of the color information corresponding to the excitation light can be avoided in the normal observation and the special light observation.

Here, the intensity of the autofluorescence of the subject and/or the fluorescence of the agents imaged in the fluorescence observation is extremely weak even compared to that of the reflected/scattered light of the white light imaged in the normal observation. Therefore, in the case where the solid-state imaging device 50 is driven in the same way in both of the fluorescence observation and normal observation, the average intensity of the image signals output from the solid-state imaging device 50 in the fluorescence observation is lower than that in the normal observation. Therefore, in the electronic endoscope 1, the intensity difference in imaging signal is compensated by the gain control circuit 53 contained in the imaging unit 43.

In the normal observation and fluorescence observation, in the light source unit 3, the CPU 32 alternatively turns on the first light source 30 and the second light source 31. The CPU 56 provided in the endoscope body 2 communicates with the CPU 32 provided in the light source unit 3, and synchronizes with the CPU 32 to change the amplification ratio of the gain control circuit 53 between the time when the first light source 30 is turned on and the time when the second light source 31 is turned on, i.e. between the normal observation and the fluorescence observation. The amplification ratio of the gain control circuit 53 is set higher in the fluorescence observation than in the normal observation. The intensity difference between the imaging signal output from the solid-state imaging device 50 in the normal observation and those in the fluorescence observation is compensated.

In the above-mentioned example, the gain correction is performed for the imaging signals before the A/D conversion, but it is also possible to perform the gain correction in the image processing section 60 of the processor unit 4 for the imaging signals which have already been converted to digital signals by the A/D converter 54.

As described above, in the primary-color-based imaging element, the G filter is made thicker, while in a complementary-color-based imaging element, it is preferable to make either or both of the Y filter and the G filter thicker as described above.

With respect to the above-mentioned fluorescence observation of autofluorescence, when the fluorescence produced from the fluorescence materials such as collagen contained in the living body by applying the excitation light (390 nm to 470 nm) is observed, the produced fluorescence is extremely weak compared to the applied excitation light. Therefore, selectively lowering the sensitivity to the excitation light component makes detection of the weak fluorescence component be reliable, and more accurate endoscope diagnosis become possible. For the fluorescence observation of autofluorescence, there is also a technology in which tumorous lesions and normal mucous membranes are highlighted with different color tones by applying light at a wavelength which is absorbed by the hemoglobins in blood (540 nm to 560 nm). In this electronic endoscope 1, by appropriately providing necessary light sources in the light source unit 3, various fluorescence observations become possible.

Next, the detection of agent fluorescence will be described. In this case, the fluorescence to be detected is the fluorescence from agents. For the pixels provided with the R filters sensitive to that fluorescence, the sensitivity to excitation light is lowered.

For example, there is a photodynamic diagnosis (PDD) in which malignant tumor sites are specified by administering fluorescent agents with an affinity for malignant tumors to a living body, applying light having a certain wavelength after the fluorescent agents have been selectively accumulated in the tumorous tissues, and observing the produced fluorescence. Examples of fluorescent agents in this case include photofrin, laserphyrin, and 5-ALA. Table 1 shows the excitation light wavelengths for the agents and the wavelengths of the produced fluorescences. As shown in Table 1, no matter which fluorescent agent of photofrin, laserphyrin, and 5-ALA is used, the blue laser light having the center wavelength of 405 nm may be used as the excitation light. In consideration of combinations with other fluorescent agents not given as examples, the wavelength of the excitation light is preferably within the range of 390 to 410 nm.

TABLE 1

| agent name | excitation wavelength | fluorescence wavelength | PDT treatment light wavelength |
| --- | --- | --- | --- |
| Photofrin | 405 nm | 630 nm | 630 nm |
| Laserphyrin | 405 nm | 670 nm | 664 nm |
| 5-ALA | 405 nm | 636 nm | 630 nm |

Furthermore, it is also possible to detect both of the above-mentioned autofluorescence and the agent fluorescence simultaneously with the imaging device. That is to say, when blue laser light is applied as the excitation light, autofluorescence from the living tissues thus obtained is detected by the pixels provided with the G filters, and the agent fluorescence caused by the agents administered to the living body is detected by the pixels provided with the R filters. In this case, because image in formation obtained by detecting the autofluorescence and image information obtained by detecting the agent fluorescence are from the same imaging device, the image information can be aligned with each other with high precision, and more accurate diagnosis is possible. Furthermore, because the image information are displayed simultaneously, the change manner of the lesion and the like can be observed in realtime.

Figure 7:
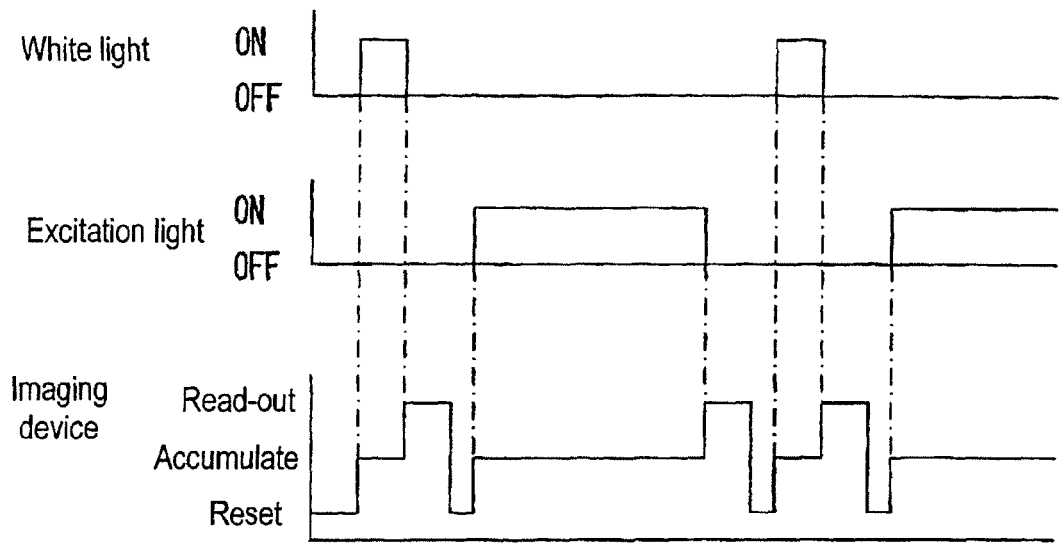
FIG. 7 is a diagram which conceptually illustrates a modification example of the electronic endoscope shown in FIG. 1.

FIG. 7 conceptually illustrates a modification example of the electronic endoscope 1.

In the example shown in FIG. 7, the charge accumulation time in the plurality of pixels 70 contained in the solid-state imaging device 50 in the normal observation is different from that in the fluorescence observation. Thus, the intensity difference between imaging signals output from the solid-state imaging device 50 in the normal observation and those in the fluorescence observation can be compensated.

As shown in FIG. 7, the frame rate, that is, the reading-out period of the charges accumulated respectively in the plurality of pixels 70 contained in the solid-state imaging device 50, when the excitation light is applied in the fluorescence observation, is made lower or shorter than that when the white light is applied in the normal observation. Therefore, the charge accumulation time in the pixels 70 when the excitation light is applied is longer than that when the white light is applied, and even for the autofluorescence of the subject or the fluorescence of the agents which are inferior in intensity compared to the reflected/scattered light of the white light, enough charges are accumulated in the pixels 70. Thus, the intensity difference between the imaging signals output from the solid-state imaging device 50 in the normal observation and those in fluorescence observation can be compensated.

Figure 8:
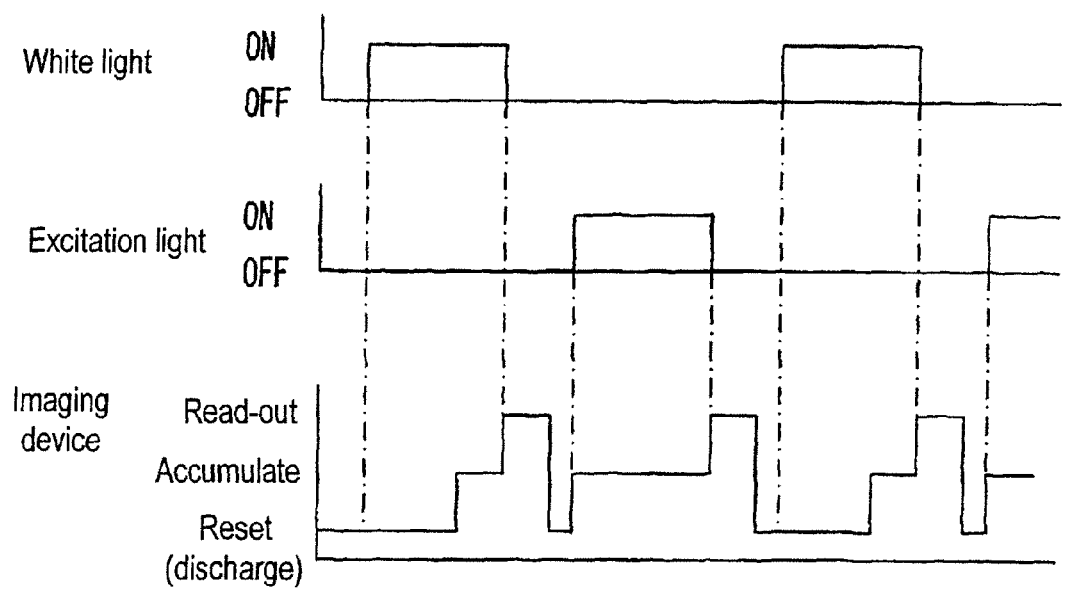
FIG. 8 is a diagram which conceptually illustrates another modification example of the electronic endoscope shown in FIG. 1.

FIG. 8 conceptually illustrates another modification example of the electronic endoscope 1.

In the example shown in FIG. 8, the charge accumulation time in the plurality of pixels 70 contained in the solid-state imaging device 50 in the normal observation is also different from that in the fluorescence observation, and the intensity difference between imaging signals output from the solid-state imaging device 50 in the normal observation and those in the fluorescence observation is compensated, but the frame rate when the white light is applied in the normal observation is the same as that when the excitation light is applied in the fluorescence observation.

As shown in FIG. 8, during the period when the white light is applied in the normal observation, the charges produced respectively in the plurality of pixels 70 contained in the solid-state imaging device 50 are discharged for a predetermined time shorter than that period. On the other hand, during the period when the excitation light is applied in the fluorescence observation, charges are accumulated into the pixels 70 throughout the entire period without the charged being discharged. Therefore, the charge accumulation time in the pixels 70 when the excitation light is applied is longer than that when the white light is applied, and even for the autofluorescence of the subject or the fluorescence of the agents which are inferior in intensity compared to the reflected/scattered light of the white light, enough charges are accumulated in the pixels 70. Thus, the intensity difference between the imaging signals output from the solid-state imaging device 50 in the normal observation and those in the fluorescence observation can be compensated.

Figure 9:
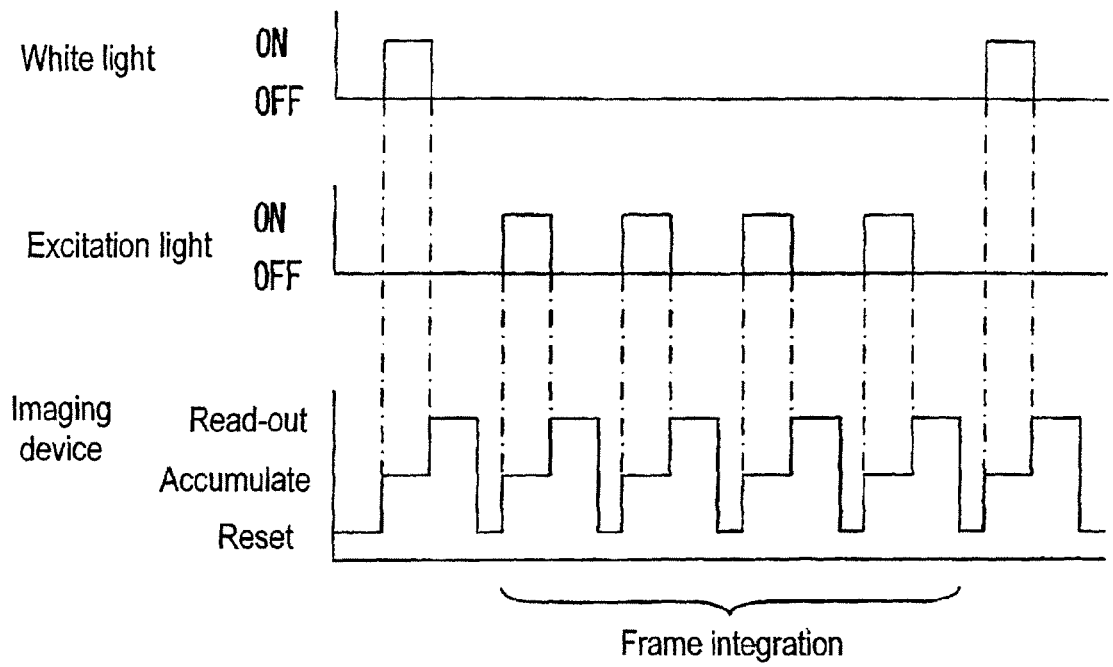
FIG. 9 is a diagram which conceptually illustrates further another modification example of the electronic endoscope shown in FIG. 1.

FIG. 9 conceptually illustrates further another modification example of the electronic endoscope 1.

In the example shown in FIG. 9, by performing frame integration when the excitation light is applied, the intensity difference between the imaging signals output from the solid-state imaging device 50 in the normal observation and those in the fluorescence observation is compensated. In the image processing portion 61 of the processor unit 4 (see FIG. 2), a frame memory capable of holding, for example, at least imaging signals for one frame is provided.

As shown in FIG. 9, when the white light is applied in the normal observation, the image processing portion 61 of the processor unit 4 (see FIG. 2) generates image data based on the imaging signals for one frame output from the solid-state imaging device 50. Meanwhile, when the excitation light is applied in the fluorescence observation, the image processing portion 61 integrates successively imaging signals for plural frames output consecutively from the solid-state imaging device 50 with using the frame memory, and generates image data based on the integrated imaging signals. Thus, the intensity difference between the imaging signals output from the solid-state imaging device 50 in the normal observation and those in the fluorescence observation can be compensated.

Figure 10:
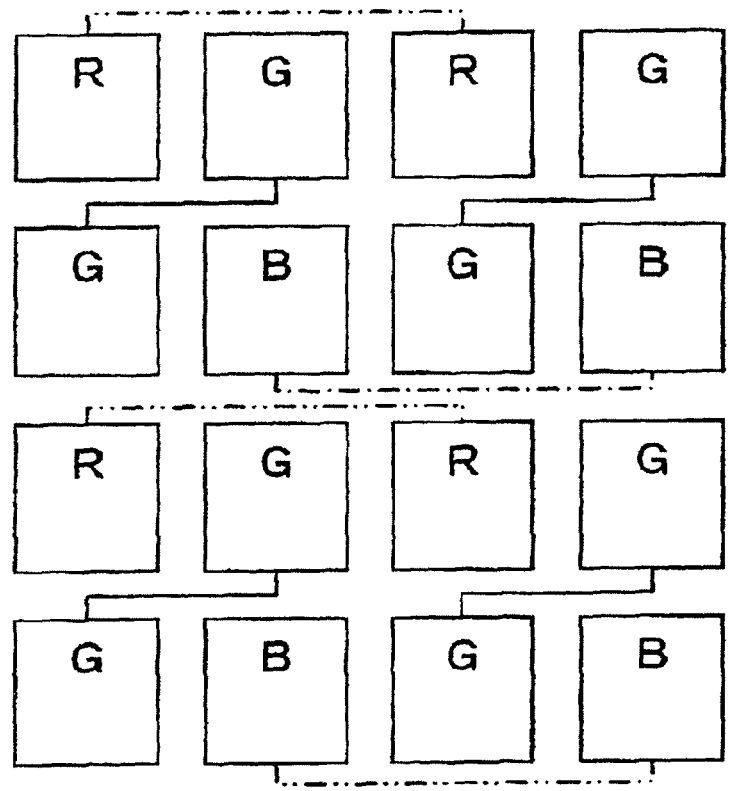
FIG. 10 is a diagram which conceptually illustrates still further another modification example of the electronic endoscope shown in FIG. 1.

FIG. 10 conceptually illustrates still further another modification example of the electronic endoscope 1.

In the example shown in FIG. 10, by performing pixel mixture when the excitation light is applied, the intensity difference between the imaging signals output from the solid-state imaging device 50 in the normal observation and those in the fluorescence observation is reduced.

When the white light is applied in the normal observation, the solid-state imaging device 50 reads out the charges accumulated in the plurality of pixels 70 contained therein pixel by pixel. Meanwhile, as shown in FIG. 10, when the excitation light is applied in the fluorescence observation, the charges accumulated in adjacent pixels 70 provided with filters of the same color among the plurality of pixels 70 are added (mixed) to be read out as a whole. Thus, the intensity difference between the imaging signals output from the solid-state imaging device 50 in the normal observation and those in the fluorescence observation can be reduced. In this case, the resolution of the images obtained in the fluorescence observation is lower than that obtained in the normal observation, but the fluorescence is inherently somewhat blur, and it is enough to show the area of the lesion part, so there is no problem.

The above-mentioned pixel mixture is described premised on that it is performed by a circuit for reading out the charges from the pixels 70. However, the pixel mixture may be performed in the image processing section 60. Below, the pixel mixture in the image processing section 60 will be described.

Figure 12:
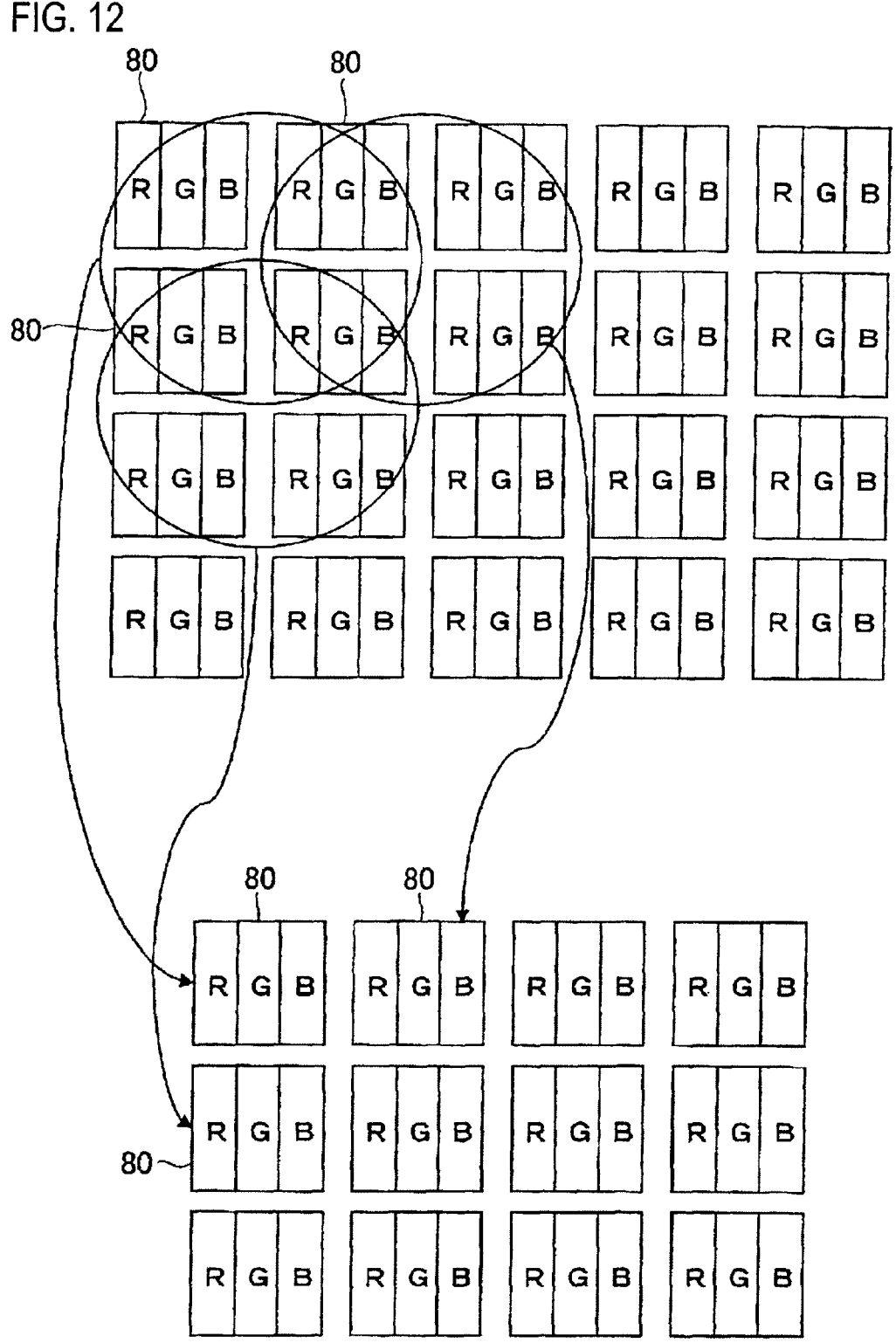
FIG. 12 is a diagram which conceptually illustrates still further another modification example of the electronic endoscope shown in FIG. 1.

FIG. 11 schematically illustrates the structure of the image data generated by the image processing section 60, and FIG. 12 conceptually illustrates the pixel mixture in the image processing section 60.

The image data are composed of a set of plural pixels 80. Each of the pixels 71 contained in the solid-state imaging device 50 has only brightness information of the color corresponding to the color filter 76 provided thereon, i.e. one of red (R), green (G), and blue (B). However, by performing operations to supplement each of the pixels 71 with the brightness information concerning the other colors of the surrounding pixels 71 in the image processing section 60, each of the pixels 80 composing the image data has the brightness information of the three colors of R, and B.

When the white light is applied in the normal observation, the image processing section 60 performs the supplementing processing to generate image data. Meanwhile, as shown in FIG. 12, when the excitation light is applied in the fluorescence observation, after the above-mentioned supplementing operations, the image processing section 60 further adds up the brightness values of the colors R, and B of the plurality of adjacent pixels 80 to combine them into one pixel 80, and increases the brightness values of the colors R, G, and B of the combined pixels 80. Thus, the intensity difference between the imaging signals output from the solid-state imaging device 50 in the normal observation and those in the fluorescence observation can be compensated. In the illustrated example, the adjacent 2×2 pixels are taken as one group, and the brightness values of the four pixels 80 contained therein are added up, and in the combined pixels, a brightness value of about four times is obtained. However, the invention is not limited thereto. Instead, 10×10 pixels (about 100 times), 15×15 pixels (about 225 times) may be taken as one group, or the number of the pixels 80 taken as one group may be changed according to the intensity of the imaging signals.

Furthermore, it is also possible to compensate the intensity difference between the imaging signals output from the solid-state imaging device 50 in the normal observation and those in the fluorescence observation by appropriately combining changing of charge accumulation time, frame accumulation, and pixel mixture.

As described above, an electronic endoscope of one embodiment of the invention includes an illumination unit, an imaging unit and an image generating unit. The illumination unit switches among a plurality of light beams having different spectra from each other so as to illuminate a subject. The light beams include at least white light and excitation light for exciting the subject to produce fluorescence. The imaging unit includes a solid-state imaging device and an objective optical system. The objective optical system guides, to the solid-state imaging device, light returning from the subject which the illumination unit illuminates. The image generating unit generates image data based on image signals output from the imaging unit. The solid-state imaging device further includes a sensitivity adjusting unit that only lowers sensitivity, to the excitation light, of pixels which are sensitive to the fluorescence among a plurality of pixels of the solid-state imaging device. The light guided by the objective optical system is incident directly onto the solid-state imaging device.

With the above-mentioned structure, the normal observation and the fluorescence observation are performed using a single solid-state imaging device by switching between the white light and the excitation light in the illumination section and applying one of the white light and the excitation light. By only lowering the sensitivities, to the excitation light, of the pixels which are sensitive to the fluorescence produced by the subject onto which the excitation light is applied, and making the light guided by the objective optical system incident directly onto the solid-state imaging device, the loss of the color information corresponding to the excitation light can be avoided in the normal observation, and the fluorescence can be collected while the pixel saturation caused by the excitation light in the fluorescence observation can be prevented.

Also, in the electronic endoscope of one embodiment of the invention, the sensitivity adjusting unit may include color filters provided for the plurality of pixels of the solid-state imaging device. Thicknesses of the color filters for the pixels sensitive to the fluorescence may be thicker than those of the color filters for the other pixels. By making the color filters for the pixels sensitive to the fluorescence be thicker, the sensitivity, to the excitation light, of the pixels can be lowered greatly as compared to the sensitivity, to the fluorescence, of those pixels.

In the electronic endoscope of one embodiment of the invention, the solid-state imaging device may be a primary-color-based solid-state imaging device having color filters of red, green, and blue. The color filters sensitive to the fluorescence may be those of green. The color of the excitation light to which the sensitivities may be lowered is blue.

In the electronic endoscope of one embodiment of the invention, the solid-state imaging device may be a primary-color-based solid-state imaging device having color filters of red, green, and blue. The color filters sensitive to the fluorescence may be those of red. The color of the excitation light to which the sensitivities may be lowered is blue.

In the electronic endoscope of one embodiment of the invention, the solid-state imaging device may be a primary-color-based solid-state imaging device having color filters of red, green, and blue. The color filters sensitive to the fluorescence may be those of green and red. The color of the excitation light to which the sensitivities may be lowered is blue.

In the electronic endoscope of one embodiment of the invention, the solid-state imaging device may be a complementary-color-based solid-state imaging device having color filters of cyan, magenta, yellow, and green. The color filters sensitive to the fluorescence may be those of at least one of green and yellow. The color of the excitation light to which the sensitivities are lowered may be blue.

The electronic endoscope of one embodiment of the invention may further include a drive circuit for the solid-state imaging device, wherein the drive circuit makes a charge accumulation time of each of the plurality of pixels of the solid-state imaging device when the excitation light is applied be longer than that when the white light is applied.

In the electronic endoscope of one embodiment of the invention, the drive circuit may make a frame rate when the excitation light is applied lower than that when the white light is applied.

In the electronic endoscope of one embodiment of the invention, the drive circuit may discharge charges, which are generated by each of the plurality of pixels of the solid-state imaging device during a period in which the white light is applied, for a predetermined time shorter than the period.

In the electronic endoscope of one embodiment of the invention, the image generating unit may have an integration unit. The integration unit integrates a plurality of frames of image signals of the solid-state imaging device when the excitation light is applied.

The electronic endoscope of one embodiment of the invention may further include a drive circuit for the solid-state imaging device. When the excitation light is applied, the drive circuit may add charges accumulated in a plurality of adjacent pixels provided with filters of a same color among the pixels of the solid-state imaging device, and read the accumulated charges out as a whole.

In the electronic endoscope of one embodiment of the invention, when the excitation light is irradiated, the image generating unit may add and combine brightness values of a plurality of adjacent pixels among the pixel that constitute the image data.

In the electronic endoscope of one embodiment of the invention, the imaging unit may have an amplification unit that amplifies the output signals of the solid-state imaging device. The amplification unit may make gains of the output signals when the excitation light is applied be higher than those when the white light is applied.

What is claimed is:

1. An electronic endoscope, comprising:
    an illumination unit that switches among a plurality of light beams having different spectra from each other so as to illuminate a subject, the light beams including at least white light and excitation light for exciting the subject to produce fluorescence;
    an imaging unit that includes:
        a solid-state imaging device; and
        an objective optical system that guides, to the solid-state imaging device, light returning from the subject which the illumination unit illuminates; and
    an image generating unit that generates image data based on image signals output from the imaging unit,
    wherein the solid-state imaging device includes a sensitivity adjusting unit that lowers sensitivity, to the excitation light, of only pixels which are sensitive to the fluorescence among a plurality of pixels of the solid-state imaging device, said plurality of pixels comprising said pixels which are sensitive to the fluorescence and pixels which are insensitive to the fluorescence,
    wherein the light guided by the objective optical system is incident directly onto the solid-state imaging device,
    wherein the sensitivity adjusting unit includes color filters provided for the plurality of pixels of the solid-state imaging device, and
    wherein thicknesses of the color filters for the pixels which are sensitive to the fluorescence are thicker than those of the color filters for said pixels which are insensitive to the fluorescence.

2. The electronic endoscope according to claim 1, wherein the solid-state imaging device comprises a primary-color-based solid-state imaging device comprising color filters of red, green, and blue,
    wherein the color filters sensitive to the fluorescence comprise those of green, and
    wherein the color of the excitation light to which the sensitivities are lowered comprises blue.

3. The electronic endoscope according to claim 1, wherein the solid-state imaging device comprises a primary-color-based solid-state imaging device comprising color filters of red, green, and blue,
    wherein the color filters sensitive to the fluorescence comprise those of red, and
    wherein the color of the excitation light to which the sensitivities are lowered comprises blue.

4. The electronic endoscope according to claim 1, wherein the solid-state imaging device comprises a primary-color-based solid-state imaging device comprising color filters of red, green, and blue,
    wherein the color filters sensitive to the fluorescence comprise those of green and red, and
    wherein the color of the excitation light to which the sensitivities are lowered comprises blue.

5. The electronic endoscope according to claim 1, wherein the solid-state imaging device comprises a complementary-color-based solid-state imaging device comprising color filters of cyan, magenta, yellow, and green, wherein the color filters sensitive to the fluorescence comprise those of at least one of green and yellow, and wherein the color of the excitation light to which the sensitivities are lowered comprises blue.

6. The electronic endoscope according to claim 1, further comprising:

a drive circuit for the solid-state imaging device, wherein the drive circuit makes a charge accumulation time of each of the plurality of pixels of the solid-state imaging device when the excitation light is applied be longer than that when the white light is applied.

7. The electronic endoscope according to claim 6, wherein the drive circuit makes a frame rate when the excitation light is applied lower than that when the white light is applied.

8. The electronic endoscope according to claim 6, wherein the drive circuit discharges charges, which are generated by each of the plurality of pixels of the solid-state imaging device during a period in which the white light is applied, for a predetermined time shorter than the period.

9. The electronic endoscope according to claim 1, wherein the image generating unit comprises an integration unit, and wherein the integration unit integrates a plurality of frames of image signals of the solid-state imaging device when the excitation light is applied.

10. The electronic endoscope according to claim 1, further comprising:

a drive circuit for the solid-state imaging device, wherein, when the excitation light is applied, the drive circuit adds charges accumulated in a plurality of adjacent pixels provided with filters of a same color among the pixels of the solid-state imaging device, and reads the accumulated charges out as a whole.

11. The electronic endoscope according to claim 1, wherein, when the excitation light is irradiated, the image generating unit adds and combines brightness values of a plurality of adjacent pixels among the pixel that constitute the image data.

12. The electronic endoscope according to claim 1, wherein the imaging unit comprises an amplification unit that amplifies output signals of the solid-state imaging device, and wherein the amplification unit makes gains of the output signals when the excitation light is applied be higher than those when the white light is applied.

13. The electronic endoscope according to claim 1, wherein a transmissivity of filters for the pixels sensitive to the fluorescence is less than a transmissivity of filters of said pixels which are insensitive to the fluorescence.

14. The electronic endoscope according to claim 1, further comprising:

a light receiving element, wherein less amount of the excitation light reaches the light receiving element from filters for the pixels sensitive to the fluorescence than filters for said pixels which are insensitive to the fluorescence.

15. The electronic endoscope according to claim 1, wherein a filter is provided on only said pixels which are sensitive to the fluorescence.

* * * * *